United States Patent [19]

McCain

[11] Patent Number: 4,524,236

[45] Date of Patent: Jun. 18, 1985

[54] PROCESS FOR OXYDEHYDROGENATION OF ETHANE TO ETHYLENE

[75] Inventor: James H. McCain, Charleston, W. Va.

[73] Assignee: Union Carbide Corporation, Danbury, Conn.

[21] Appl. No.: 625,777

[22] Filed: Jun. 28, 1984

[51] Int. Cl.³ ............................ C07C 5/38; C07C 5/48
[52] U.S. Cl. .................................... 585/658; 502/312; 502/315; 502/316; 502/317; 502/324; 502/337; 502/338; 502/340; 502/343; 502/344; 502/349; 502/353
[58] Field of Search .............. 585/658, 656; 502/311, 502/312, 315, 316, 317, 328, 329, 330, 353, 340, 344, 324, 337, 338, 343, 349

[56] References Cited

U.S. PATENT DOCUMENTS

| | | | |
|---|---|---|---|
| 3,845,156 | 10/1974 | Farha | 585/658 |
| 3,933,933 | 1/1976 | Bertus | 585/658 |
| 3,972,954 | 8/1976 | Bertus | 585/658 |
| 4,020,120 | 4/1977 | Christmann et al. | 585/658 |
| 4,044,066 | 8/1977 | Ripley | 585/658 |
| 4,051,193 | 9/1977 | Kurtz et al. | 585/658 |
| 4,067,922 | 1/1978 | Foster | 585/658 |
| 4,083,884 | 4/1978 | Purdy | 585/658 |
| 4,148,757 | 4/1979 | Brazdil et al. | 252/432 |
| 4,150,064 | 4/1979 | Miklas | 585/658 |
| 4,167,532 | 9/1979 | Walker et al. | 585/658 |
| 4,250,346 | 2/1981 | Young et al. | 585/658 |
| 4,339,355 | 7/1982 | Decker et al. | 252/464 |
| 4,410,752 | 10/1983 | Blum et al. | 585/658 |

OTHER PUBLICATIONS

"The Oxidative Dehydrogenation of Ethane Over Catalyst Containing Mixed Oxide of Molybdenum and Vanadium: by E. M. Thorsteinson, T. P. Wilson, F. G. Young and P. H. Kasai, *Journal of Catalyst* 52, pp. 226–243, (1978).

*Primary Examiner*—Delbert E. Gantz
*Assistant Examiner*—Anthony McFarlane
*Attorney, Agent, or Firm*—David Fink

[57] ABSTRACT

A process for the low temperature oxydehydrogenation of ethane to ethylene uses a calcined oxide catalyst containing Mo, V, Nb, Sb, and at least one metal from a given group of metals.

4 Claims, No Drawings

1

PROCESS FOR OXYDEHYDROGENATION OF ETHANE TO ETHYLENE

FIELD OF THE INVENTION

The invention relates to a process for low temperature oxydehydrogenation of ethane to ethylene, and particularly to a process using an improved catalyst featuring good conversion and good selectivity.

BACKGROUND OF THE INVENTION

Low temperature oxydehydrogenation of ethane to ethylene has become well known since the publication of "The Oxidative Dehydrogenation of Ethane over Catalyst Containing Mixed Oxide of Molybdenum and Vanadium" by E. M. Thorsteinson, T. P. Wilson, F. G. Young and P. H. Kasai, *Journal of Catalysis* 52, pp. 116–132 (1978). This article discloses mixed oxide catalysts containing molybdenum and vanadium together with another transition metal oxide (Ti, Cr, Mn, Fe, Co, Ni, Nb, Ta, or Ce). The catalysts are active at temperatures as low as 200° C. for the oxydehydrogenation of ethane to ethylene.

The effectiveness of the oxydehydrogenation of ethane to ethylene is usually primarily determined by two parameters: conversion of ethane, and selectivity (efficiency) to ethylene. As used herein, these terms are defined as follows:

$$\text{conversion of ethane} = \frac{[CO]/2 + [CO_2]/2 + [C_2H_4]}{[CO]/2 + [CO_2]/2 + [C_2H_4] + [C_2H_6]}$$

$$\text{selectivity (efficiency) to ethylene} = \frac{[C_2H_4]}{[CO]/2 + [CO_2]/2 + [C_2H_4]}$$

wherein: [ ]=relative moles of the component and the production of acetic acid is negligible. The terms in the art are sometimes calculated differently but the values calculated either way are substantially by the same.

Under certain reaction conditions, substantial amounts of acetic acid can be formed as a co-product and the effectiveness of the reaction to ethylene and acetic acid is calculated by the following equations:

$$\text{conversion of ethane} = \frac{[CO]/2 + [CO_2]/2 + [C_2H_4] + [CH_3COOH]}{[CO]/2 + [CO_2]/2 + [C_2H_4] + [C_2H_6] + [CH_3COOH]}$$

$$\text{selectivity (efficiency) to ethylene and acetic acid} = \frac{[C_2H_4] + [CH_3COOH]}{[CO]/2 + [CO_2]/2 + [C_2H_4] + [C_2H_6] + [CH_3COOH]}$$

U.S. Pat. No. 4,250,346 discloses catalytic oxydehydrogenation of ethane to ethylene at temperatures less than 550° C. in which the catalyst is a calcined composition comprising the elements Mo, X, and Y in the ratio $$Mo_aX_bY_c$$

wherein:
X=Cr, Mn, Nb, Ta, Ti, V, and/or W.
Y=Bi, Ce, Co, Cu, Fe, K, Mg, Ni, P, Pb, Sb, Si, Sn, Tl, and/or U.
a=1
b=0.05 to 1.0
c=0 to 2

The numerical values of a, b, and c represent the relative gram-atom ratios of the elements Mo, X, and Y, respectively, which are present in the catalyst composition. The elements Mo, X, and Y are present in the catalyst composition in combination with oxygen.

The patent discloses a wide variety of compositions; however, all of the examples of the patent which include antimony, examples 27, 28, and 41, disclosed very poor results. Example 27 had a catalyst having a composition $V_3Sb_{12}Ce_1$ and resulted in no selectivity for the formation of ethylene. Example 28 had catalyst having a composition $Sb_5V_1Nb_1Bi_5$ and had an initial activity at 525° C. with a selectivity of only 26%. Example 41 had a catalyst having a composition of $Mo_{16}V_4Sb_2$ which provided a conversion of 6% with a selectivity of 95% at 300° C., and a conversion of 23% and a selectivity of 75% at 400° C.

U.S. Pat. No. 4,339,355 discloses a catalytic oxide of molybdenum, vanadium, niobium, and a fourth metal which is Co, Cr, Cu, Fe, In, Mn and/or Y. The patent discloses that the catalyst is suitable for the vapor phase catalytic oxidation of unsaturated aliphatic aldehydes to the corresponding saturated aliphatic carboxylic acid.

U.S. Pat. No. 4,148,757 discloses catalysts for the oxidation and/or ammoxidation of olefins. The patent is particularly directed to a novel process for producing oxidation and/or ammoxidation catalysts and sets forth the following general formula for such catalyst:

$$[M_mN_nO_x]q[A_a, C_b, D_c, E_d, F_e, N_f, O_y]p$$

wherein:
M=Bi, Te, Sb, Sn, and/or Cu
N=Mo and/or W
A=alkali, Tl, and/or Sm
C=Ni, Co, Mn, Mg, Be, Ca, Si, Ba, Zn, Cd, and/or Hg
D=Fe, Cr, Ce, and/or V
E=P, AS, B, Sb
F=rare earth, Ti, Zr, Nb, Ta, Re, Ru, Ag, Au, Al, Ga, In, Si, Ge, Pb, Th, and/or U
a=0 to 4
b=0 to 20
c=0.01 to 20
d=0 to 4
e=0 to 8
f=8 to 16
m=0.10 to 10
n=0.1 to 30, and
x and y are numbers such that the valence requirements of the other elements for oxygen are satisfied; and the ratio q/p is 0.1 to 10.

None of the catalysts disclosed in U.S. Pat. No. 4,148,757 are disclosed as being suitable for the oxydehydrogenation of ethane to ethylene. Moreover, the suitability of the catalyst for olefins teaches away from the use of the catalysts for the oxydehydrogenation of ethane to ethylene because it would be expected that the ethylene would be oxygenated.

SUMMARY OF THE INVENTION

The present invention relates to a process for the low temperature catalytic oxydehydrogenation of ethane to ethylene in a gas phase and features the use of a catalyst having a calcined composition of $Mo_aV_bNb_cSb_dX_e$ wherein:

x = at least one of the following: Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, and W; and a = 0.5 to 0.9
b = 0.1 to 0.4
c = 0.001 to 0.2
d = 0.001 to 0.1.
e = 0.001 to 1.0

The values of a, b, c, d and e constitute relative gram-atoms of the elements Mo, V, Nb, Sb, and X respectively, in the catalyst. The elements are present in combination with oxygen in a form of various oxides.

DISCUSSION OF THE INVENTION

The catalyst of the invention can be used with or without a support. The choice of the compounds used as well as the specific procedures followed in preparing a catalyst can have a significant effect on the performance of a catalyst. The elements of the catalyst composition are in combination with oxygen as oxides.

Preferably, the catalyst is prepared from a solution of soluble compounds and/or complexes and/or compounds of each of the metals. The solution is preferably an aqueous system having a pH of 1 to 12 and more preferably a pH of 5±3, at a temperature of from about 20° C. to about 100° C.

Generally, a mixture of compounds containing the elements is prepared by dissolving sufficient quantities of soluble compounds and dispersing the insoluble compounds so as to provide a desired gram-atom ratios of the elements in the catalyst composition. The catalyst composition is then prepared by removing the water or other solvent from the mixture of the compounds in the solution system. The dried catalyst is calcined by heating to a temperature from about 220° C. to about 550° C. in air or oxygen for a period of time from about one minute to about 24 hours to produce the desired catalyst composition. Generally, the higher the temperature the shorter the period of time required.

Suitable supports for the catalyst include silica, aluminum oxide, silicon carbide, zirconia, titania, and mixtures thereof. When used on a support, the supported catalyst usually comprises from about 10 to 50% by weight of the catalyst composition, with the remainder being the support.

Preferably, the molybdenum is introduced into the solution in the form of ammonium salts such as ammonium paramolybdate, or organic acid salts of molybdenum such as acetates, oxalates, mandelates, and glycolates. Some other partially water soluble molybdenum compound which may be used include molybdenum oxides, molybdic acid, and chlorides of molybdenum.

Preferably, the vanadium is introduced into the solution in the form of ammonium salts such as ammonium meta-vanadate and ammonium decavanadate, or organic acid salts of vanadium such as acetates, oxalates, and tartrates. Partially water soluble vanadium compounds such as vanadium oxides, and sulfates of vanadium can be used.

Preferably, the niobium and tantalum, when used, are in the form of oxalates. Other sources of these metals in soluble form include compounds in which the metal is coordinated, bonded or complexed to a beta-diketonate, carboxylic acid, and amine, and alcohol, or an alkanolamine.

Preferably, the antimony is introduced into solution in the form of antimony oxalate. Other soluble and insoluble compounds of antimony can be used such as antimony oxide and antimony chloride.

The X component of the catalyst can be soluble or insoluble compounds, preferably soluble. Compounds which are strongly reducing may adversely reduce the oxidation states of the metals.

The following are some preferable compounds for the X components. One is titanium in the form of a water soluble chelate coordinated with ammonium lactate, and others are titanium compounds in which the metal is coordinated, or complexed to a beta-diketonate, a carboxylic acid, an amine, an alcohol or an alkanolamine. Generally, nitrates are desirable along with water soluble chlorides and organic acid salts such as acetates, oxalates, tartrates, lactates, salicylates, formates, and carbonates. Preferred compounds for tungsten are in the form of ammonium salts such as ammonium paratungstate or other water soluble compounds such as tungstic acids.

Preferably, the catalyst is prepared by the following general procedure. The vanadium compound is mixed with water to form a first solution or suspension, the niobium, and antimony, are mixed with water to form a second solution or suspension, and molybdenum compound is mixed with water to form a third solution or suspension. Any X compounds which are ammonium salts are mixed with the first solution. Otherwise, X compounds are mixed into the second solution. The first and second solutions are heated separately and mixed for about fifteen minutes; and then combined and mixed with heating for about fifteen minutes. The third solution is heated and mixed, and then added to the combined first and second solutions to form a combined solution. After mixing and heating of the combined solutions for about fifteen minutes, the combined solution is evaporated to dryness rapidly in air usually, but the drying could be carried out in an inert atmosphere.

When the catalyst is to be used with a support, it is believed desirable to filter the combined solution to remove the insoluble portion before impregnating the support. The filtering can be carried out using sintered glass, or a paper filter with or without suction.

It has been found that catalyst surface area and activity depend on the digestion time, i.e., the time taken to evaporate the combined solution to dryness. Compositions allowed to digest for relatively long periods of time, thirty minutes or more, before drying at 120° C. generally undergo particle growth with loss in surface area.

It is believed that the catalyst for the invention should have one or more of the metal components slightly below their highest possible oxidation states. The calcining is carried out with the flow of air or some other oxygen containing gas over the dry solids prepared from the solutions to control the reducing actions of reducing agents such as $NH_3$ or organic reducing agents which are introduced into the solution system from which the catalysts are prepared. The rate of flow of the gas can be determined experimentally for the apparatus and the quantities of solids being used for optimizing the properties of the catalyst being produced.

One or more of the free valances of metals in the catalyst are occupied by one or more of oxide, hydroxyl, and $CO_3$.

In general, the catalyst, supported or unsupported can be used in a fixed or fluidized bed.

The raw material used as the source of the ethane can be a gas stream which contains at least three volume percent of ethane. The gas stream can also contain minor amounts of hydrogen, carbon monoxide, and the $C_3$–$C_4$ alkanes and alkenes, less than five volume percent of each. The gas stream can also contain major amounts, more than five volume percent, of nitrogen, methane, carbon dioxide, and water in the form of steam.

The catalyst of the invention is substantially limited to the oxydehydrogenation of ethane to ethylene because the catalyst does not efficiently oxydehydrogenate propane, n-butane, and butene-1, but medaminantly burns these gases to carbon dioxide and other oxidized carbonaceous products.

The reaction mixture in carrying out the process is generally one mol of ethane, 0.01 to 1.0 mol of molecular oxygen either as pure oxygen or in the form of air, and zero to 4.0 mol of water in the form of steam. The water or steam is used as a reaction diluent and as a heat moderator for the reaction. Other gases may be used as reaction diluent or heat moderators such as nitrogen, helium, carbon dioxide, and methane.

During the course of the reaction, one mol of water is formed for each mol of ethane that is oxydehydrogenated. The water from the reaction results in the formation of some acetic acid. Under several atmospheres of pressure, about 0.05 to 0.25 mol of acetic acid per mol of ethylene is formed.

The water that is added to the feed stream will also cause the formation of additional amounts of acetic acid, up to about 0.25 to 1.0 mol of acetic acid per mol of ethylene that is formed.

The gaseous components of the reaction mixture include ethane and oxygen, and possibly a diluent, and these components are uniformally admixed prior to being introduced into the reaction zone. The components may be preheated, individually or after being admixed, prior to being introduced into the reaction zone which should have temperature of from about 200° C. to about 450° C.

The reaction zone generally has a pressure of from about 1 to 30 atmospheres and preferably 1 to 20 atmospheres; a temperature of from about 150° C. about to 450° C., and preferably from about 200° C. to about 400° C.; a contact time between the reaction mixture and the catalyst of from about 0.1 to about 100, and preferably from about 1 to 10 seconds; and a space velocity of from about 50 to 5000 $h^{-1}$, and preferably 200 to 3000 $h^{-1}$.

The contact time is defined as the ratio between the apparent volume of the catalyst bed and the volume of the gaseous reaction mixture feed to the catalyst bed under the given reaction conditions in a unit of time.

The space velocity is calculated by determining total reactor outlet gas equivalent in liters of the total effluent evolved over a period of one hour divided by the liters of catalyst in the reactor. This room temperature volume is converted to the volume at 0° C. at 760 mm Hg;

$$\text{space velocity} = \frac{\text{liters of outlet gas equivalents per hour}}{\text{liters of catalyst in reactor}} = h^{-1}$$

The reaction pressure is initially provided by the feed of the gaseous reactant and diluent and after the reaction has commenced, the pressure is maintained, preferably, by the use of suitable back-pressure controllers placed on the reactor outlet stream.

The reaction temperature is preferably provided by placing the catalyst bed within a tubular converter having walls immersed in a suitable heat transfer medium such as tetralin, molten salt mixtures, or other suitable heat transfer agents heated to the desired reaction temperature.

Generally, the process can be carried out in a single stage with all of the oxygen for the reaction being supplied along with an inert diluent. It is desirable to operate without a diluent to facilitate the isolation of the ethylene produced. When a diluent is not used this presents several problems because a large amount of oxygen can create a hazardous condition and the uncontrolled presence of water and acetic acid can adversely affect the production of ethylene. Accordingly, it is believed that the use of multiple stages improves the process. Multiple stages allows the oxygen needed for the total reaction of the ethane to be introduced at various stages and thereby avoid a potentially hazardous condition.

Surprisingly, the supply of oxygen in various stages rather than a supply of the total amount of the oxygen in the initial stage has no detrimental affect on the production of ethylene. In addition, the use of stages enables the control of the amount of water present in stages subsequent to the first stage. If desired, water can be withdrawn and thereby minimize the formation of acetic acid.

It is desirable to compare the performance of the instant catalysts with prior art catalysts. Optimally, a comparison should be made for the same set of conditions and the same equipment. This is not always convenient or economically justified.

A reasonably good basis for comparing catalyst performance can be achieved by comparing selectivity to ethylene for the same conversion of ethane. This can be accomplished easily by taking advantage of the discovered substantially linear relationship between selectivity to ethylene and conversion of ethane over the useable operating temperature range. Thus, it is unnecessary to actually operate at the conversion of ethane being used for a comparison because one can interpolate or extrapolate to any desired set of values from two sets of data.

EXAMPLES

Several examples were carried out to demonstrate the invention and compare it to the prior art.

The process for the various catalysts were carried out in a tubular reactor under the following conditions:

Gas feed composition was 8% by volume ethane, 6.5% by volume oxygen, and 85.5% by volume helium. The space velocity was about 720 $h^{-1}$ at a one atmosphere total pressure. The reactor consisted of a 9 millimeter diameter stainless steel straight tube heated in an oven with a blower and at a temperature of from 330° C. to 425° C. The reactor contained 2.5 grams of the catalyst. The reactor bed depth was about 6.0 centimeters so that the depth to cross section ratio was about seven. The liquid products, water and traces of acetic acid, were condensed in a trap and the gaseous products were analyzed for oxygen and carbon monoxide at 65° C. on a 3 m×3 mm column of 5 A molecular sieve (60/80 mesh). An analysis at 65° C. was carried out for carbon dioxide, ethylene, and ethane on a 1.8 m×3 mm column of material sold under the trademark POROPAK Q (50/80 mesh). In all cases, the conversion and selectivity calculations were based on the Stoichiometry:

$$C_2H_6 + \tfrac{1}{2}O_2 \rightarrow C_2H_4 + H_2O$$

$$C_2H_6 + 5/2 O_2 \rightarrow 2CO + 3H_2O$$

$$C_2H_6 + 7/2 O_2 \rightarrow 2CO_2 + 3H_2O$$

EXAMPLE 1

A catalyst was prepared to have the following composition:

$$Mo_{0.61}V_{0.26}Nb_{0.07}Sb_{0.04}Ca_{0.02}$$

Ammonium metavanadate in the amount of 9.90 grams (0.085 gram atom of V) was added to 100 ml of water and heated to 70° C. with stirring for fifteen minutes. Niobium oxalate amounting to 31.1 grams of solution containing 10% by weight calculated as $Nb_2O_5$ (0.0234 gram atom of Nb), antimony (III) oxalate amounting to 3.12 grams (0.0123 gram-atom of Sb) and calcium nitrate tetrahydrate amounting to 1.46 grams (0.0062 gram-atom of Ca) were added to a second 100 ml of water and heated to 70° C. with stirring for fifteen minutes. The second mixture was combined with the first mixture and the combination was heated at 70° C. with stirring for fifteen minutes. To a third 100 ml of water was added 35.3 grams (0.200 gram-atom of Mo) of ammonium paramolybdate. This mixture was heated to 70° C. with stirring for fifteen minutes and then added to the combined mixtures. The final mixture was heated at 70° C. and stirred for fifteen minutes.

The resulting mixture was evaporated to dryness in air with stirring in steam-heated stainless steel evaporating dish. The resulting solid was broken and sieved to an 8×30 mesh and dried additionally in an oven at 120° C. for sixteen hours. The dried material was transferred to three separate 100 cc beakers and calcined in an oven equipped with a blower at a temperature of 350° C. The temperature was raised from room temperature to 350° C. over a period of twenty minutes and thereafter held at 350° C. for five hours.

The catalysts was tested according to the above described test and the results are shown in Table II.

EXAMPLE 2

Using the procedure of Example 1, a catalyst having the following composition was prepared:

$$Mo_{0.60}V_{0.25}Nb_{0.07}Sb_{0.04}Ca_{0.04}$$

The same amounts of compounds were used except that 2.92 grams of calcium nitrate tetrahydrate (0.0124 gram-atom of Ca) was used so that the catalyst produced had a higher calcium content than he catalyst of Example 1. The results of the tests with this catalyst are given in Table II.

EXAMPLE 3

Using the procedure of Example 2, a catalyst having the following composition was prepared:

$$Mo_{0.62}V_{0.26}Nb_{0.07}Sb_{0.04}Ca_{0.01}$$

The same amounts of compounds were used except that 0.73 gram of calcium nitrate (0.0031 gram atom of Ca) was used so that the catalyst produced had a lower calcium content than the catalyst of Example 1. The results of the tests with this catalyst are given in Table II.

EXAMPLES 4 TO 28

Examples 4 to 28 were carried out using the same procedure as used in Example 1 with the same quantities of the compounds used for Mo, V, Nb, and Sb. The X component was varied and in some cases several metals. Table I shows the X component, X salt, weight of the X salt, gram-atom of the X metal, and the composition of the catalysts for Examples 4 to 28. The results of the tests with these catalysts are given in Table II.

TABLE I

| Ex. | X | X Salt | Wt. (g.) | gram-atom | Catalyst Composition |
|---|---|---|---|---|---|
| 4 | Sr | nitrate | 1.31 | 0.0062 | $Mo_{.61}V_{.26}Nb_{.07}Sb_{.04}Sr_{.02}$ |
| 5 | Mg | nitrate.6 $H_2O$ | 1.59 | 0.0062 | $Mo_{.61}V_{.26}Nb_{.07}Sb_{.07}Mg_{.02}$ |
| 6 | Bi | nitrate | 2.97 | 0.0062 | $Mo_{.61}V_{.26}Nb_{.07}Sb_{.04}Bi_{.02}$ |
| 7 | La, Na | nitrates | 1.34, 0.26 | 0.0031, 0.0031 | $Mo_{.61}V_{.26}Nb_{.07}Sb_{.04}La_{.01}Na_{.01}$ |
| 8 | Ba | nitrate | 1.62 | 0.0062 | $Mo_{.61}V_{.26}Nb_{.07}Sb_{.04}Ba_{.02}$ |
| 9 | Pb | nitrate | 2.05 | 0.0062 | $Mo_{.61}V_{.26}Nb_{.07}Sb_{.04}Pb_{.02}$ |
| 10 | Ni | nitrate | 1.00 | 0.0062 | $Mo_{.61}V_{.26}Nb_{.07}Sb_{.04}Ni_{.02}$ |
| 11 | Li | nitrate | 0.42 | 0.0062 | $Mo_{.61}V_{.26}Nb_{.07}Sb_{.04}Li_{.02}$ |
| 12 | Co(II) | nitrate.6 $H_2O$ | 1.80 | 0.0062 | $Mo_{.61}V_{.26}Nb_{.07}Sb_{.04}Co_{.02}$ |
| 13 | Zn | nitrate | 1.18 | 0.0062 | $Mo_{.61}V_{.26}Nb_{.07}Sb_{.04}Zn_{.02}$ |
| 14 | Ce(III) | nitrate | 2.69 | 0.0062 | $Mo_{.61}V_{.26}Nb_{.07}Sb_{.04}Ce_{.02}$ |
| 15 | Cd, Mn | nitrates | 1.92, 1.95 of 50% aqueous solution | 0.0062, 0.0088 | $Mo_{.61}V_{.26}Nb_{.07}Sb_{.04}Cd_{.02}Mn_{.03}$ |
| 16 | Cr(III) | nitrate.6 $H_2O$ | 2.48 | 0.0062 | $Mo_{.61}V_{.26}Nb_{.07}Sb_{.04}Cr_{.02}$ |
| 17 | Bi | nitrate | 5.94 | 0.062 | $Mo_{.61}V_{.26}Nb_{.07}Sb_{.04}Bi_{.04}$ |
| 18 | Na | nitrate | .53 | 0.0062 | $Mo_{.61}V_{.26}Nb_{.07}Sb_{.04}Na_{.02}$ |
| 19 | Cd | nitrate | 1.92 | 0.0062 | $Mo_{.61}V_{.26}Nb_{.07}Sb_{.04}Cd_{.02}$ |
| 20 | Fe(III) | nitrate | 2.50 | 0.0062 | $Mo_{.61}V_{.26}Nb_{.07}Sb_{.04}Fe_{.02}$ |
| 21 | La | nitrate.9 $H_2O$ | 2.68 | 0.0062 | $Mo_{.61}V_{.26}Nb_{.07}Sb_{.04}La_{.02}$ |
| 22 | Hg(II) | nitrate | 2.28 | 0.0062 | $Mo_{.61}V_{.26}Nb_{.07}Sb_{.04}Hg_{.02}$ |
| 23 | Al | nitrate.9 $H_2O$ | 2.33 | 0.0062 | $Mo_{.61}V_{.26}Nb_{.07}Sb_{.04}Al_{.02}$ |
| 24 | Sb(II) | oxalate | 1.28 | 0.0062 | $Mo_{.61}V_{.26}Nb_{.07}Sb_{.04}SbII_{.02}$ |
| 25 | Fe(II) | oxalate | 1.12 | 0.0062 | $Mo_{.61}V_{.26}Nb_{.07}Sb_{.04}Fe_{.02}$ |
| 26 | K | nitrate | 0.63 | 0.0062 | $Mo_{.61}V_{.26}Nb_{.07}Sb_{.04}K_{.02}$ |
| 27 | Rb | nitrate | 0.91 | 0.0062 | $Mo_{.61}V_{.26}Nb_{.07}Sb_{.04}Rb_{.02}$ |
| 28 | Ce | nitrate | 1.21 | 0.0062 | $Mo_{.61}V_{.26}Nb_{.07}Sb_{.04}Ce_{.02}$ |

EXAMPLE 29

Using the procedure of Example 1, a catalyst having the following composition was prepared:

$Mo_{0.62}V_{0.26}Nb_{0.07}Sb_{0.04}Mn_{0.01}Cd_{0.02}W_{0.01}U_{0.01}Ce_{0.0004}Pb_{0.01}$

The same amounts of the compounds for Mo, V, Nb, and Sb were used as in Example 1. Ammonium tungstate in the amount of 0.92 gram (0.0035 gram-atom W) and ammonium diuranate in the amount of 0.68 gram (0.0021 gram-atom of U) were mixed with the ammonium metavanadate solution. Cerium (III) nitrate in the amount of 0.05 gram (0.0001 gram-atom Ce), cadmium nitrate in the amount of 1.63 grams (0.0053 gram-atom of Cd), lead (II) nitrate in the amount of 0.76 gram (0.0023 gram-atom of Pb) and manganese (II) nitrate in the amount of 1.04 grams of a 50% aqueous solution (0.0029 gram-atom of Mn) were mixed with the niobium oxalate and antimony oxalate solution. The results of the tests with this catalyst are given in Table II.

TABLE II

| Ex. | X Metal | Temp. °C. | Conversion of Ethane | Selectivity to Ethylene |
|---|---|---|---|---|
| 1 | Ca | 330 | 34 | 86 |
|  |  | 350 | 55 | 76 |
|  |  | 375 | 66 | 73 |
|  |  | 400 | 73 | 71 |
| 2 | Ca | 340 | 33 | 86 |
|  |  | 350 | 53 | 77 |
|  |  | 375 | 65 | 72 |
|  |  | 400 | 76 | 66 |
| 3 | Ca | 340 | 32 | 86 |
|  |  | 350 | 41 | 80 |
|  |  | 375 | 64 | 62 |
|  |  | 400 | 68 | 73 |
| 4 | Sr | 340 | 32 | 86 |
|  |  | 350 | 47 | 79 |
|  |  | 375 | 57 | 77 |
|  |  | 400 | 71 | 71 |
| 5 | Mg | 340 | 30 | 87 |
|  |  | 350 | 39 | 79 |
|  |  | 375 | 52 | 77 |
|  |  | 400 | 67 | 74 |
| 6 | Bi | 344 | 33 | 86 |
|  |  | 358 | 51 | 78 |
|  |  | 375 | 63 | 75 |
|  |  | 400 | 74 | 69 |
| 7 | La, Na | 350 | 32 | 86 |
|  |  | 375 | 48 | 75 |
|  |  | 400 | 62 | 72 |
| 8 | Ba | 350 | 31 | 86 |
|  |  | 375 | 57 | 77 |
|  |  | 400 | 71 | 71 |
| 9 | Pb | 335 | 31 | 86 |
|  |  | 350 | 49 | 74 |
|  |  | 375 | 62 | 73 |
|  |  | 400 | 73 | 69 |
| 10 | Ni | 340 | 38 | 83 |
|  |  | 375 | 61 | 72 |
|  |  | 400 | 70 | 69 |
| 11 | Li | 350 | 32 | 85 |
|  |  | 375 | 44 | 79 |
|  |  | 400 | 58 | 75 |
| 12 | Co | 330 | 31 | 85 |
|  |  | 350 | 46 | 79 |
|  |  | 375 | 61 | 73 |
|  |  | 400 | 70 | 70 |
| 13 | Zn | 330 | 30 | 86 |
|  |  | 350 | 44 | 77 |
|  |  | 375 | 59 | 71 |
|  |  | 400 | 69 | 69 |
| 14 | Ce | 350 | 27 | 86 |
|  |  | 375 | 54 | 75 |
|  |  | 400 | 65 | 71 |
| 15 | Cd | 344 | 30 | 84 |
|  |  | 350 | 42 | 78 |
|  |  | 375 | 55 | 74 |
|  |  | 400 | 66 | 69 |
| 16 | Cr | 350 | 33 | 83 |
|  |  | 375 | 47 | 76 |
|  |  | 400 | 61 | 71 |
| 17 | Bi | 350 | 34 | 82 |
|  |  | 375 | 50 | 75 |
|  |  | 400 | 65 | 70 |
| 18 | Na | 357 | 30 | 86 |
|  |  | 375 | 47 | 80 |
|  |  | 400 | 61 | 75 |
| 19 | Cd | 343 | 32 | 85 |
|  |  | 375 | 51 | 80 |
|  |  | 400 | 66 | 73 |
| 20 | Fe(III) | 353 | 35 | 83 |
|  |  | 375 | 44 | 72 |
|  |  | 400 | 60 | 69 |
| 21 | La | 355 | 30 | 85 |
|  |  | 385 | 56 | 76 |
|  |  | 405 | 63 | 74 |
| 22 | Hg | 340 | 32 | 84 |
|  |  | 400 | 66 | 66 |
| 23 | Al | 353 | 30 | 84 |
|  |  | 375 | 40 | 75 |
|  |  | 400 | 54 | 72 |
| 24 | Sb(II) | 360 | 29 | 79 |
|  |  | 375 | 36 | 74 |
|  |  | 400 | 49 | 70 |
| 25 | Fe(II) | 350 | 25 | 74 |
|  |  | 375 | 38 | 71 |
|  |  | 400 | 52 | 68 |
| 26 | K | 350 | 23 | 78 |
|  |  | 370 | 32 | 82 |
|  |  | 400 | 44 | 76 |
| 27 | Rb | 350 | 19 | 78 |
|  |  | 375 | 28 | 78 |
|  |  | 383 | 32 | 81 |
|  |  | 400 | 41 | 76 |
| 28 | Mn, Cd, W, U, Ce, Pb | 345 | 30 | 86 |
|  |  | 375 | 58 | 76 |
|  |  | 400 | 70 | 72 |

I claim:

1. In a low temperature process for converting ethane to ethylene by catalytically oxydehydrogenating ethane exothermically at a temperature of from about 150° C. to about 450° C. in the gas phase, the improvement comprises using a calcined catalyst containing $Mo_aV_bNb_cSb_dX_e$ in the form of oxides
wherein:
X = at least one of the following: Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, and W; and
a = 0.5 to 0.9
b = 0.1 to 0.4
c = 0.001 to 0.2
d = 0.001 to 0.1
e = 0.001 to 1.0.

2. The process of claim 1, wherein the selectivity to ethylene is greater than 65% for a 50% conversion of ethane.

3. The process of claim 1, wherein the selectivity to ethylene is greater than 75% for a 50% conversion of ethane.

4. The process of claim 1, wherein X further comprises Mn in the amount of 0.001 to 1.0.